(12) United States Patent
Siegenthaler

(10) Patent No.: US 11,439,405 B2
(45) Date of Patent: Sep. 13, 2022

(54) SURGICAL CLIP FOR SIMULTANEOUS BLEEDING CONTROL OF A BLOOD VESSEL AND CUTTING

(71) Applicant: Michael Siegenthaler, Potomac, MD (US)

(72) Inventor: Michael Siegenthaler, Potomac, MD (US)

( * ) Notice: Subject to any disclaimer, the term of this patent is extended or adjusted under 35 U.S.C. 154(b) by 63 days.

(21) Appl. No.: 16/539,074

(22) Filed: Aug. 13, 2019

(65) Prior Publication Data

US 2020/0046360 A1 Feb. 13, 2020

Related U.S. Application Data

(60) Provisional application No. 62/718,114, filed on Aug. 13, 2018.

(51) Int. Cl.
*A61B 17/122* (2006.01)
*A61B 17/128* (2006.01)
*A61B 17/12* (2006.01)

(52) U.S. Cl.
CPC .......... *A61B 17/122* (2013.01); *A61B 17/128* (2013.01); *A61B 2017/12004* (2013.01); *A61B 2017/1225* (2013.01)

(58) Field of Classification Search
CPC . A61B 17/122; A61B 17/128; A61B 17/1227; A61B 17/1285; A61B 2017/1225; A61B 2017/12004; A61B 17/1222; A61B 17/072; A61F 5/0086; A61F 6/20; A61F 6/202; A61F 6/206
USPC ................................ 606/158, 122, 157, 120
See application file for complete search history.

(56) References Cited

U.S. PATENT DOCUMENTS

| 4,979,950 | A | * | 12/1990 | Transue | A61B 17/122 606/158 |
| 5,591,173 | A | | 1/1997 | Schifano | |
| 5,797,922 | A | * | 8/1998 | Hessel | A61B 17/122 606/120 |
| 5,913,862 | A | * | 6/1999 | Ramsey | A61B 17/122 606/120 |
| 5,925,052 | A | * | 7/1999 | Simmons | A61B 17/128 606/120 |
| 6,217,590 | B1 | * | 4/2001 | Levinson | A61B 17/1285 606/139 |
| 9,775,623 | B2 | * | 10/2017 | Zammataro | A61B 17/1285 |

(Continued)

FOREIGN PATENT DOCUMENTS

DE 20 2007 003 398 U1 7/2007

OTHER PUBLICATIONS

International Search Report and Written Opinion dated Nov. 7, 2019 in PCT/US19/46362, 14 pages.

*Primary Examiner* — Tan-Uyen T Ho
*Assistant Examiner* — Bridget E. Rabaglia
(74) *Attorney, Agent, or Firm* — Oblon, McClelland, Maier & Neustadt, L.L.P.

(57) ABSTRACT

A surgical clip for simultaneously cutting a blood vessel and controlling bleeding, includes two legs, each including a flat surface and a cutting surface, and a curved section configured to join the two legs. An applicator for installing a surgical clip that simultaneously divides a blood vessel and controls bleeding, includes two jaws that simultaneously hold two surgical clips, and two handles that cause the two jaws to exert a deforming force on the two surgical clips.

13 Claims, 14 Drawing Sheets

(56) References Cited

U.S. PATENT DOCUMENTS

| | | | |
|---|---|---|---|
| 10,292,712 B2* | 5/2019 | Shankarsetty | A61B 17/1285 |
| 2003/0074009 A1* | 4/2003 | Ramsey | A61B 17/122 |
| | | | 606/120 |
| 2003/0191477 A1* | 10/2003 | Qiu | A61B 17/122 |
| | | | 606/120 |
| 2006/0100649 A1 | 5/2006 | Hart | |
| 2009/0171380 A1* | 7/2009 | Whiting | A61B 17/122 |
| | | | 606/158 |
| 2013/0226200 A1* | 8/2013 | Kappel | A61B 17/1285 |
| | | | 606/142 |
| 2014/0236170 A1* | 8/2014 | Kethman | A61B 17/122 |
| | | | 606/120 |
| 2015/0048142 A1* | 2/2015 | Scheib | A61B 17/068 |
| | | | 227/180.1 |
| 2015/0080914 A1 | 3/2015 | Roundy et al. | |
| 2015/0250474 A1 | 9/2015 | Abbott et al. | |
| 2015/0359538 A1 | 12/2015 | Yeatts, II | |

\* cited by examiner

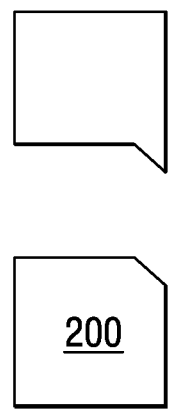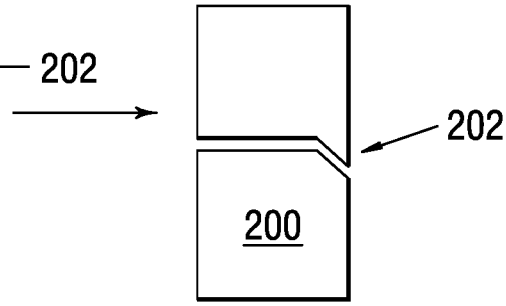
*FIG. 4A*   *FIG. 4B*
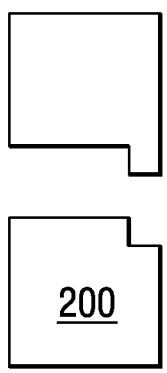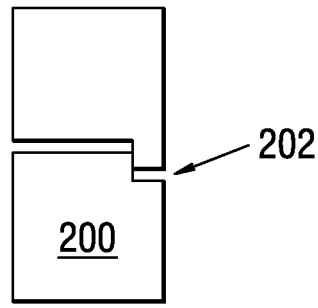
*FIG. 4C*   *FIG. 4D*

SURGICAL CLIP FOR SIMULTANEOUS BLEEDING CONTROL OF A BLOOD VESSEL AND CUTTING

CROSS-REFERENCE TO RELATED APPLICATIONS

This application claims the benefit for priority from provisional application No. 62/718,114 filed Aug. 13, 2018, the entire contents of which are incorporated herein by reference.

BACKGROUND

Field

The present disclosure is directed to surgical clips used to prevent or control bleeding during surgical procedures. Specifically, the present disclosure is directed to surgical clips that simultaneously cut blood vessels and control bleeding.

Description of the Related Art

Surgical clips are implantable devices that may be made from metals, such as stainless steel, titanium, tantalunum, platinum, or an alloy of metals, or made from polymer materials. Surgical clips have been in use since the first half of the twentieth century and have gained widespread use among different surgical disciplines with the advent of minimally invasive surgical procedures.

During surgery, a surgical clip is deployed using a clip applicator, which is a surgical instrument that places the surgical clip at a desired location, typically a blood vessel, and deforms the surgical clip into its final shape in order to occlude the blood vessel. The clip applicator has scissor-like handles and a plier-like tip, which both holds the surgical clip in its open position and exerts a force on the surgical clip in order to deform the surgical clip into its final, closed position.

Once a surgical clip is placed on a blood vessel and closed in order to occlude the lumen of the blood vessel, the blood vessel may be safely divided without the risk of excessive bleeding. In a typical division of a blood vessel, a surgical clip is placed at either side of the location where the blood vessel is to be divided. After placement of the surgical clips, the blood vessel is divided with, for example, scissors. This involves three separate steps: placing the first surgical clip, placing the second surgical clip, and dividing the blood vessel. Accordingly, the technician in the surgical room must hand the surgeon instruments three times, and has to load a new surgical into the clip applicator each time, which can be time consuming. For example, while harvesting a mammary artery for coronary artery bypass grafting in a skeletonized fashion, multiple small side branches of the internal mammary artery have to be divided and the three steps must be performed for each of these divisions, making the process both tedious and time consuming.

Attempts to reduce the number of steps required to divide a blood vessel include a surgical clip applicator that includes a blade flanked by a surgical clip at either side. The applicator can then simultaneously place the two clips and divide the blood vessel between the two clips. However, this solution is technically complex and requires a specialized clip applicator, and hence has not been put into practice.

SUMMARY

The present disclosure describes novel surgical clips that reduce the three steps required to divide a blood vessel with conventional surgical clips to just one step. Accordingly, the present disclosure is directed to surgical clips that simultaneously control bleeding and divide a blood vessel. The present disclosure is also directed to an applicator for the surgical clips that holds a minimum of two surgical clips and simultaneously applies both clips to the blood vessel thereby reducing the division of the blood vessel to a single step.

For example, the clip applicator according to exemplary aspects of the present disclosure includes two jaws for holding two surgical clips. After the closely adjacent surgical clips are advanced over a blood vessel that is to be divided, the applicator simultaneously closes both clips by bringing the two jaws together. The surgical clips are positioned very close to each other in order to create a scissoring action between them when the jaws of the applicator are closed. In one exemplary embodiment the surgical clips may be in contact with each other. Thus, there is no need for an extra blade, or other cutting mechanism, in the applicator. The surgical clips themselves perform both the cutting of the blood vessel and the occluding of the lumen of the blood vessel. This allows for control of bleeding on each side of the blood vessel and at the same time for cutting of the blood vessel without the need for a separate blade or separate scissors as used with conventional surgical clips.

In one exemplary aspect, a surgical clip for simultaneously cutting a blood vessel and controlling bleeding includes two legs, each including a flat surface and a cutting surface; and a curved section configured to join the two legs.

In another exemplary aspect, an applicator for installing a surgical clip that simultaneously divides a blood vessel and controls bleeding, includes two jaws configured to simultaneously hold two surgical clips, and two handles configured to cause the two jaws to exert a deforming force on the two surgical clips.

In another exemplary aspect, an applicator holds one or more clips on the outside of the middle cutting pair of clips on either or both side of the middle cutting pair of clips, in order to add additional stability and include an additional safety for the occlusion of the blood vessel and further reducing the risk of slipping of the cutting clips.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4A illustrates a cross-sectional view of surgical clips according to exemplary aspects of the present disclosure;

FIG. 4B illustrates another cross-sectional view of surgical clips according to exemplary aspects of the present disclosure;

FIG. 4C illustrates a cross-sectional view of surgical clips according to exemplary aspects of the present disclosure;

FIG. 4D illustrates a cross-sectional view of surgical clips according to exemplary aspects of the present disclosure;

DETAILED DESCRIPTION OF THE PREFERRED EMBODIMENTS

Figure 1A:
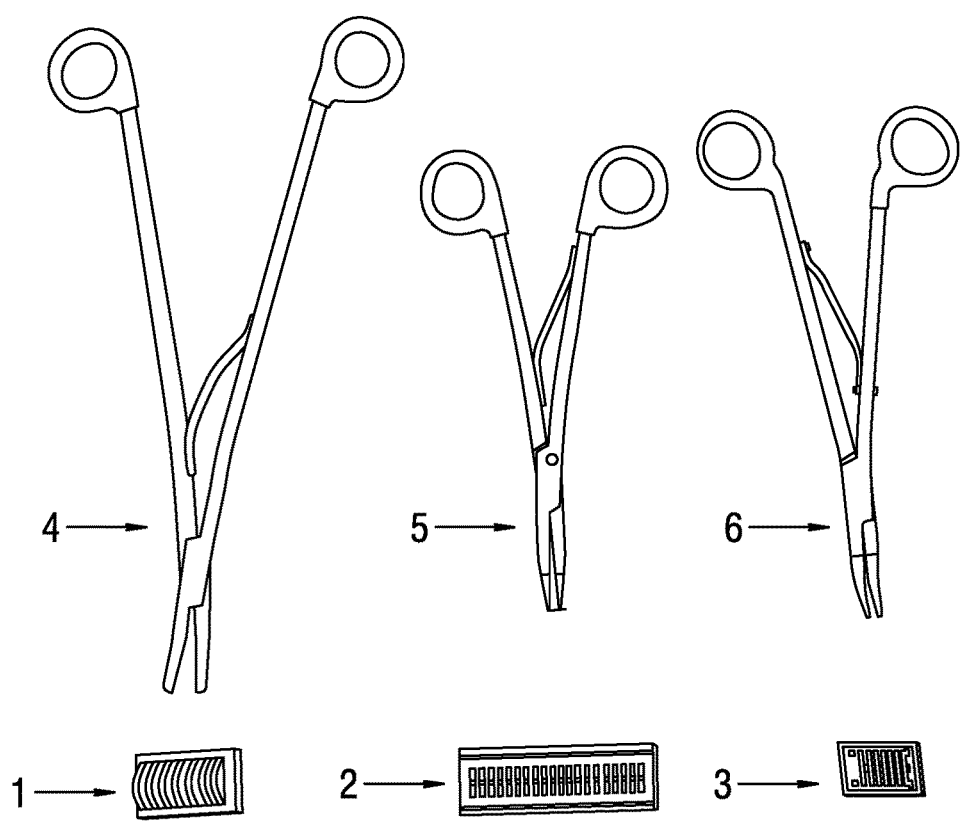
FIG. 1A illustrates conventional surgical clips of three different sizes and their respective applicators.

Referring now to the drawings, wherein like reference numerals designate identical or corresponding parts throughout the several views, FIG. 1 illustrates conventional surgical clips and their applicators. As illustrated, the surgical clips may come stacked in a carriers 1, 2, 3, and may be of different sizes to account for different application. Likewise, the applicators 4, 5, 6 for the surgical clips come in different sizes in order to accommodate the different sizes of surgical clips.

Figure 1B:
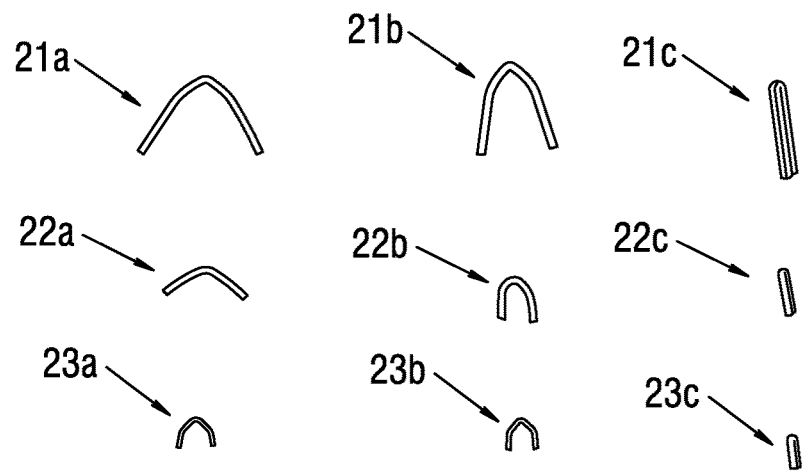
FIG. 1B illustrates three different sizes of conventional surgical clips in various states from open to closed.

FIG. 1A illustrates conventional surgical clips 21a-c, 22a-c, 23a-c of different dimensions in different states from fully open 21a-23a to fully closed 21c-23c. In FIG. 1B, the surgical clips 21 at the top is the largest, and the surgical clips 23 at the bottom is the smallest. Also, the surgical clips 21a, 22a, 23a on the left are fully open while the surgical clips 21c, 22c, 23c on the right are fully closed. The surgical clip, regardless of size, is advanced onto a blood vessel while open so that the surgical clip surrounds the blood vessel. When the surgical clip is closed, as shown on the right side of FIG. 1B (21c, 22c, 23c), the surgical clip pinches the blood vessel shut, preventing bleeding. Such clips may be left in the body after a surgical procedure. The clips may also be removed, or made of a material that can be absorbed by the body, as one of ordinary skill would recognize.

Figure 2A:
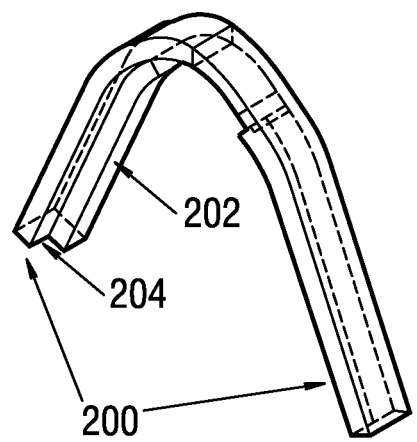
FIG. 2A is a three-dimensional view of a surgical clip according to exemplary aspects of the present disclosure.
Figure 2B:
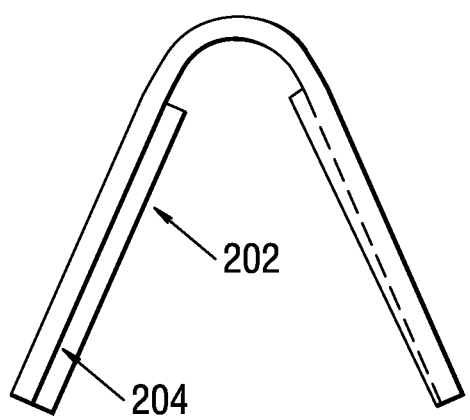
FIG. 2B is a side view of a surgical clip according to exemplary aspects of the present disclosure.
Figure 2C:
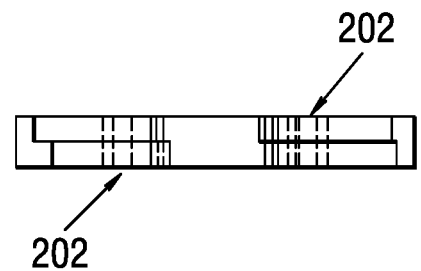
FIG. 2C is a front view of a surgical clip in a closed state according to exemplary aspects of the present disclosure.

FIG. 2A is a three-dimensional view of a surgical clip according to exemplary aspects of the present disclosure. In FIG. 2A, each leg 200 of the surgical clip includes a cutting edge 202 and a flat portion 204. The cutting edges 202 on the legs 200 of the surgical clip bypass each other to cut the blood vessel to which the surgical clip is attached by a scissoring action. FIG. 2B shows that the cutting edge 202 of each leg 200 is raised with respect to the flat portion 204 of each leg 200. As can be seen from FIG. 2C, the cutting edges 202 are on opposite sides so that when the legs 200 of the surgical clip are brought together they are able to bypass each other and perform the scissoring action.

Figure 2D:
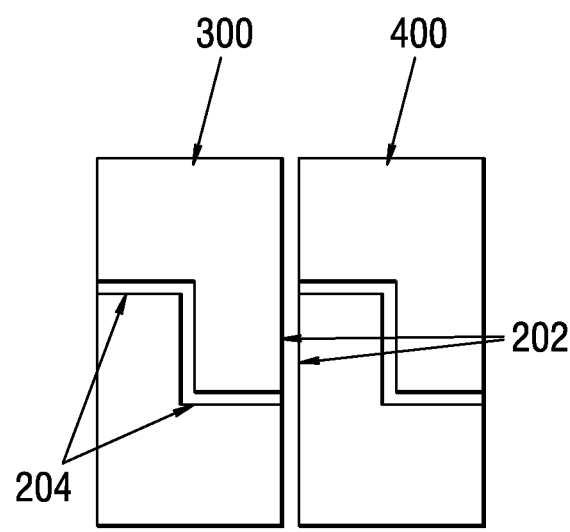
FIG. 2D is a cross-sectional view of 2 surgical clips according to exemplary aspects of the present disclosure.

FIG. 2D is a cross-sectional view of surgical clips 300 and 400 according to exemplary aspects of the present disclosure when the surgical clips 300 and 400 are in a closed state. As illustrated in this figure, when the surgical clips 300 and 400 are closed, the cutting edges 202 bypass each other to cut the blood vessel. At the same time, the flat portions 204 meet each other in order to occlude the blood vessel and prevent bleeding. As can be appreciated the cross-sectional view of FIG. 2D is merely exemplary and other cross-sectional profiles are possible without departing from the scope of the present disclosure, such as those illustrated in FIGS. 2E and 2F. As can be appreciated the exact pattern or texture applied to the surface of the flat portions 204 is not limiting upon the present disclosure, and other patterns or textures are also possible.

Figure 2E:
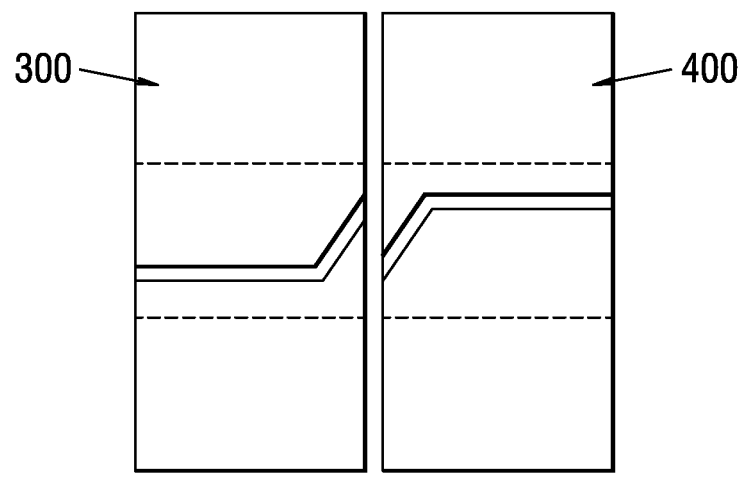
FIG. 2E is a cross-sectional view of 2 surgical clips according to exemplary aspects of the present disclosure.
Figure 2F:
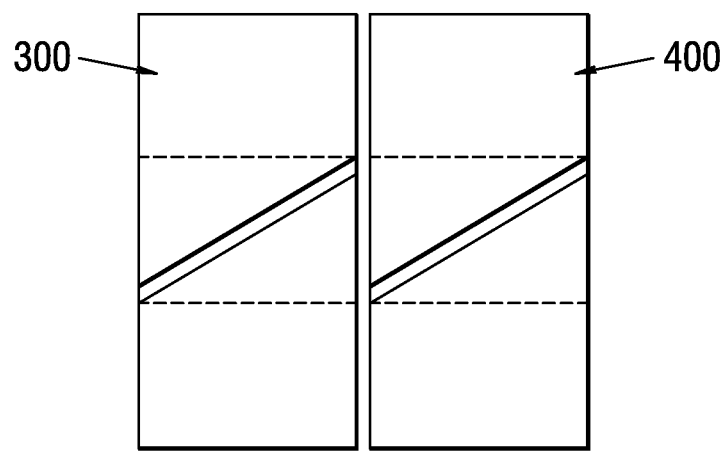
FIG. 2F is a cross-sectional view of 2 surgical clips according to exemplary aspects of the present disclosure.

Furthermore, FIGS. 2D-2F each illustrates two clips 300 and 400 side by side as they would be positioned when used to cut/clamp a blood vessel. The clips 300 and 400 may be close to each other with our without touching, and are preferably applied by a single applicator as will be explained in greater detail below. One of ordinary skill in the art will appreciate that any of the clips described herein may be used as a pair of clips as illustrated in FIGS. 2D-2F. FIGS. 2E-2F illustrate that clips 300 and 400 have the same cross-sectional profile, or cross-sectional profiles that are mirror images of each other. However, these are not requirements of the invention described in the present disclosure. As can be appreciated, the two clips 300 and 400 may have cross-sectional that are completely different from each other. As such the particular cross-sectional profile of the pair of clips used to cut/clamp a blood vessel is not limiting upon the present disclosure.

Figure 2G:
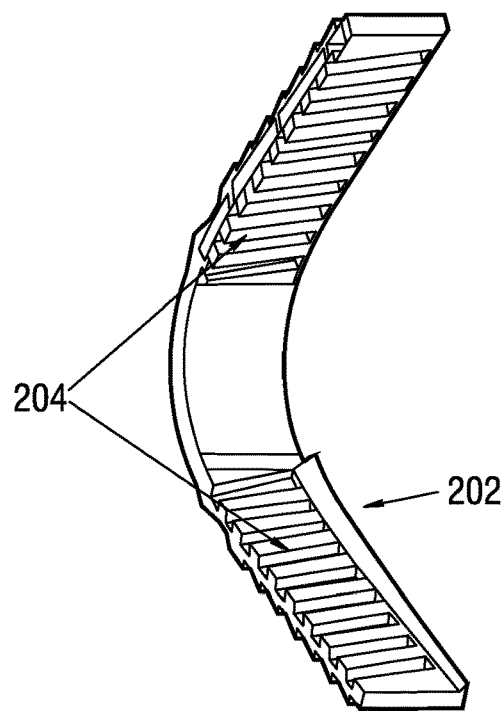
FIG. 2G is a three-dimensional view of a surgical clip according to exemplary aspects of the present disclosure.

FIG. 2G illustrates a surgical clip according to exemplary aspects of the present disclosure. The surgical clip in FIG. 2G includes a textured, or patterned, surface on the flat part 204 of each leg 200. This textured, or patterned, surface prevents slippage of the surgical clip once the clip is installed on a blood vessel. FIG. 2G also illustrates the cutting edge 202. The pattern illustrated in FIG. 2G includes a series of teeth on each of the legs 200 of the surgical clip. As can be appreciated the teeth may be made so that the teeth of one leg are offset relative to the teeth of the other leg so that they interlock with the teeth of the other leg when the clip is closed. The teeth can also be made such that the teeth of one leg align with those of the other leg so that they do not interlock when the clip is closed. Other patterns are also possible without departing from the scope of the present disclosure.

Figure 2H:
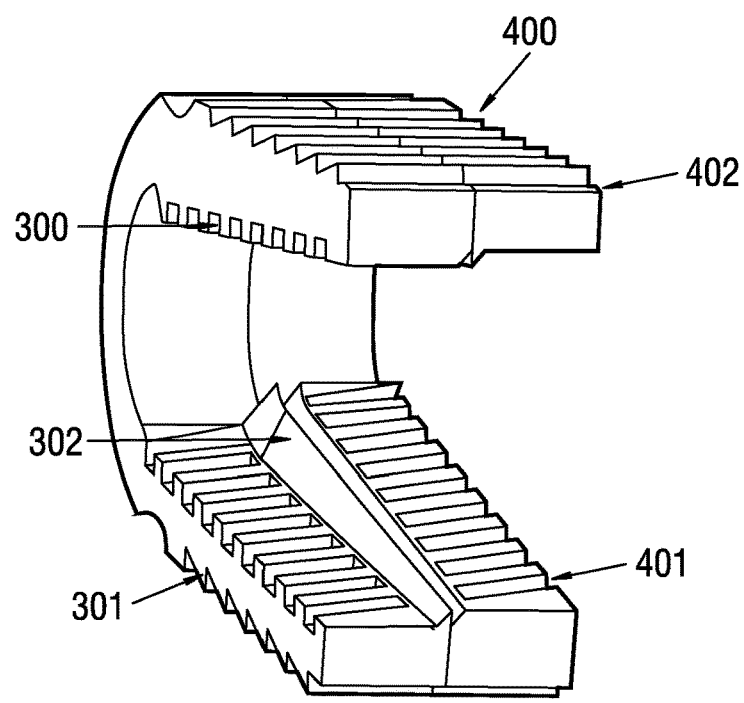
FIG. 2H is a three-dimensional view of a surgical clip according to exemplary aspects of the present disclosure.

FIG. 2H illustrates two surgical clips 300 and 400 according to exemplary aspects of the present disclosure. In FIG. 2H the surfaces of the flat portions 204 of each surgical clip 300 and 400 are textured, or patterned, as described above, as are the outer surfaces of the legs 200 of each surgical clip 300 and 400 in order to prevent slippage of the surgical clips 300 and 400 while being held by the applicator. As can be seen from this figure, the two surgical clips 300 and 400 line up such that they are able to simultaneously divide a blood vessel and seal each side of the blood vessel to prevent bleeding. Specifically, the leg 301 with the cutting edge 302 of surgical clip 300 aligns with the leg 401 without a cutting edge of the surgical clip. Similarly, the leg 402 of the surgical clip 400 with the cutting edge (not shown) aligns with the leg 303 of the surgical clip 300. In this way the two surgical clips may be placed in contact with each other and held with a same applicator so that both surgical clips 300 and 400 may be applied simultaneously to the blood vessel. Though FIG. 2H illustrates using two clips with textured surfaces, two clips without textured surfaces may also be used, or one clip with a textured surface and another clip without a textured surface may be used, as one of ordinary skill in the art would recognize.

Figure 3A:
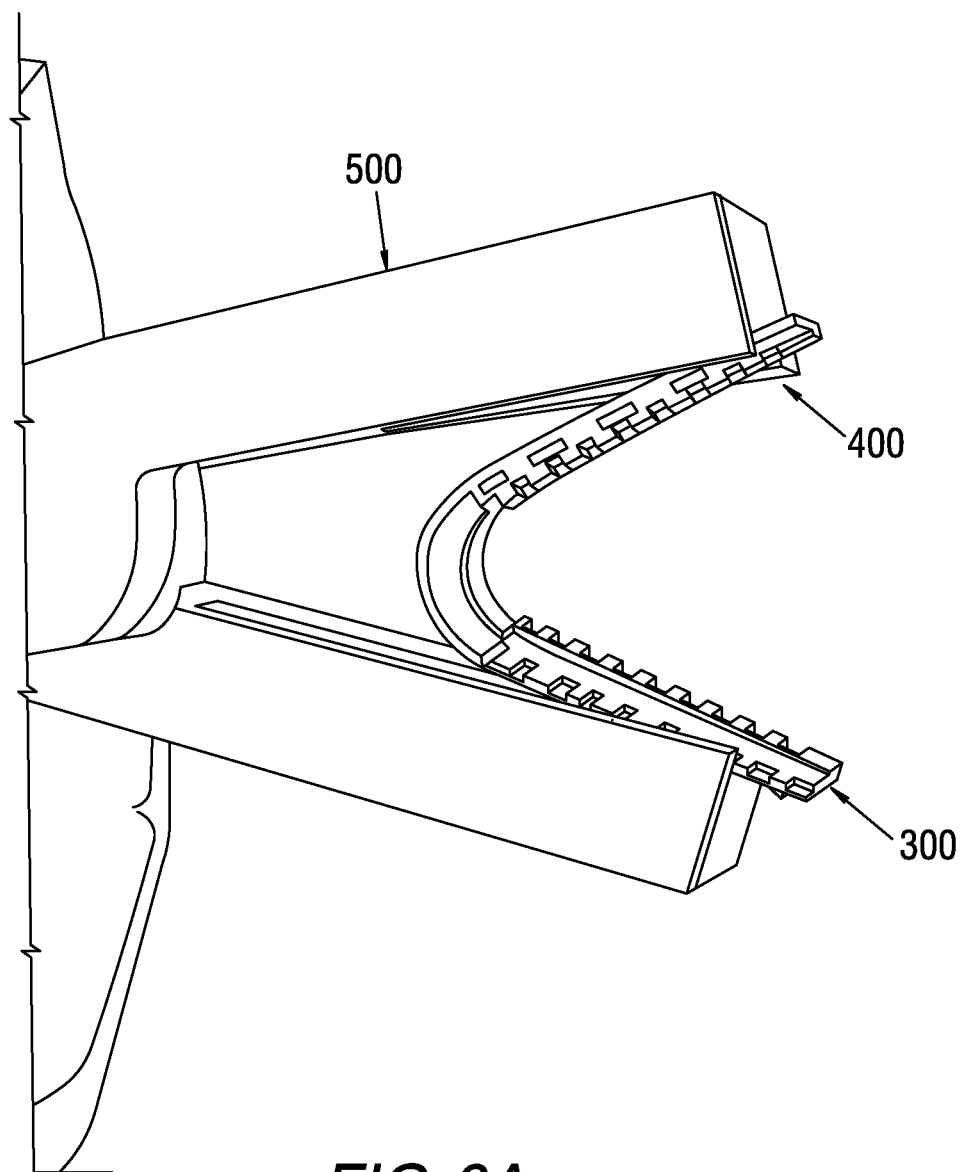
FIG. 3A is a first step in applying a surgical clip according to exemplary aspects of the present disclosure.
Figure 3B:
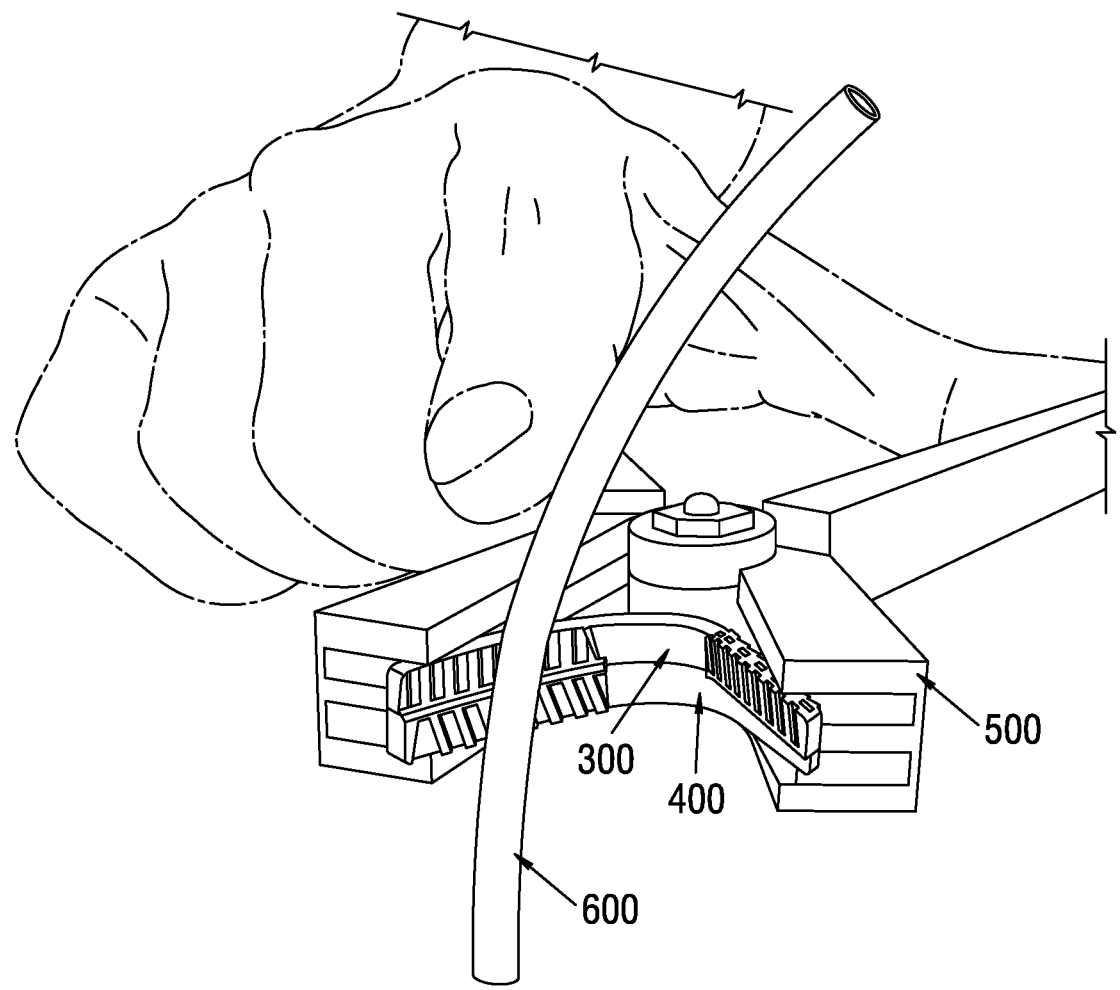
FIG. 3B is a second step in applying a surgical clip according to exemplary aspects of the present disclosure.
Figure 3C:
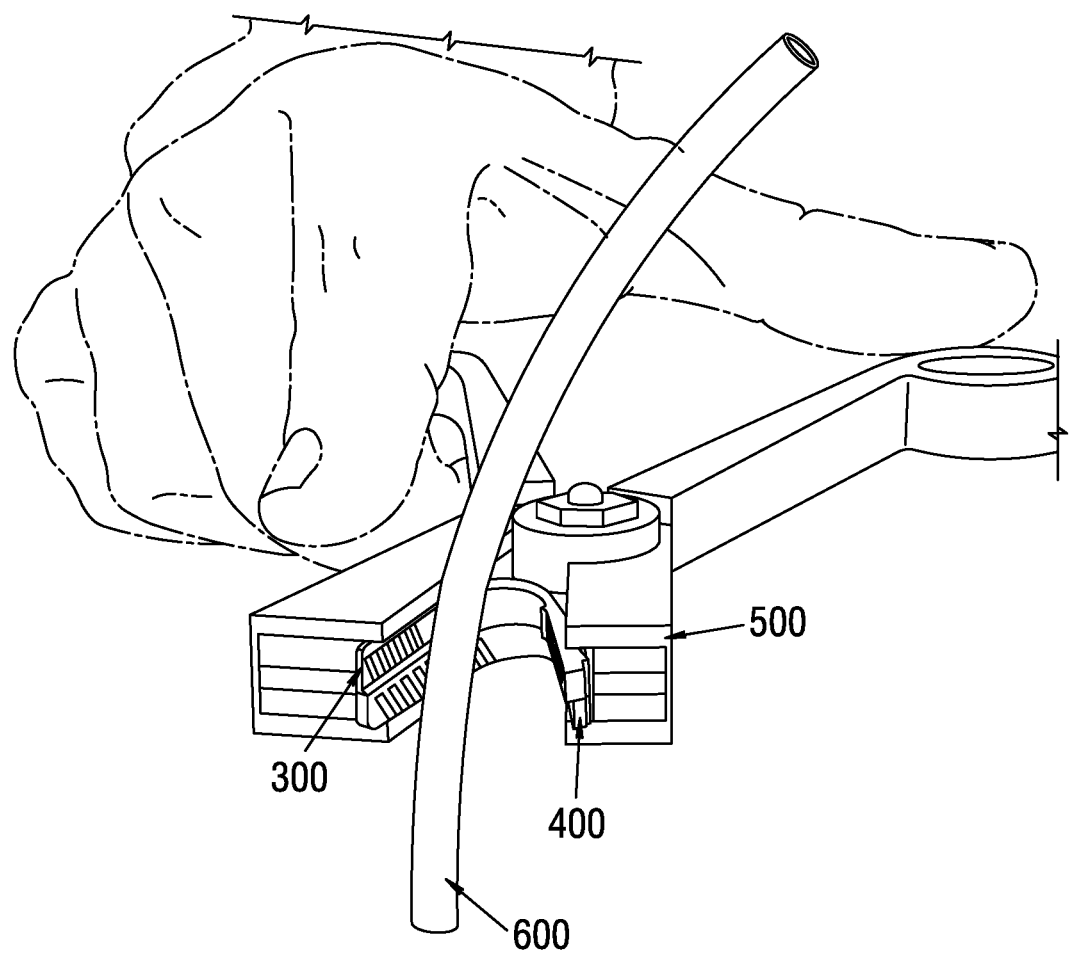
FIG. 3C is a third step in applying a surgical clip according to exemplary aspects of the present disclosure.
Figure 3D:
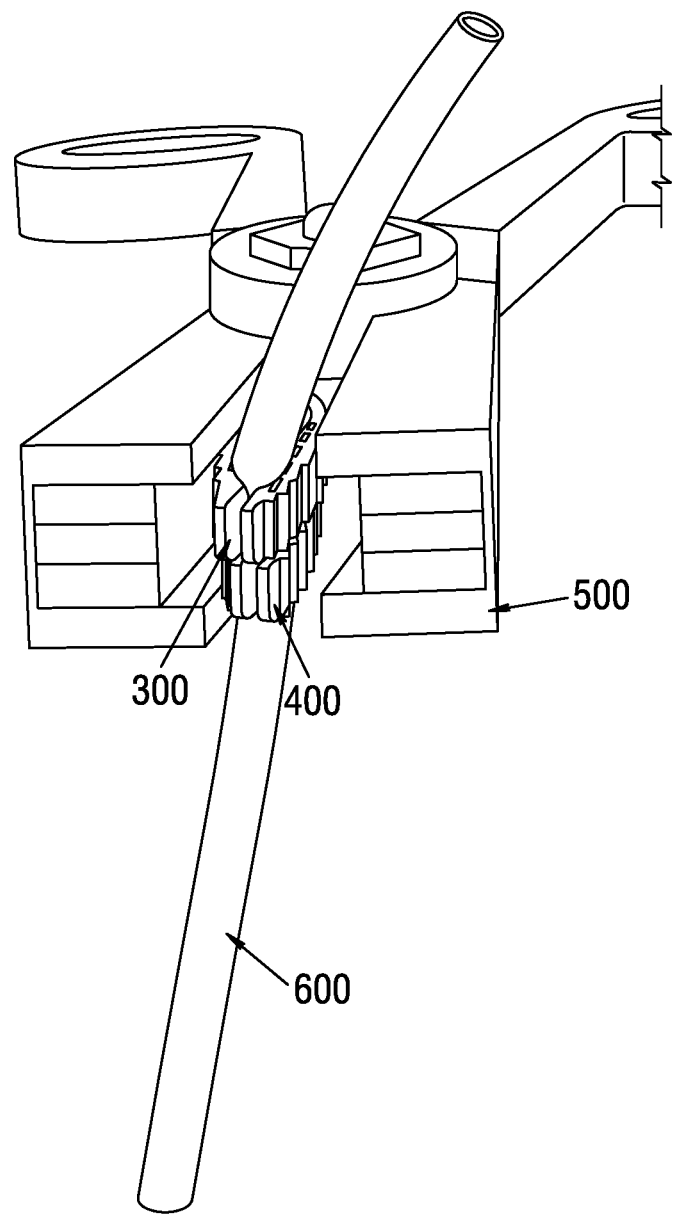
FIG. 3D is a fourth step in applying a surgical clip according to exemplary aspects of the present disclosure.
Figure 3E:
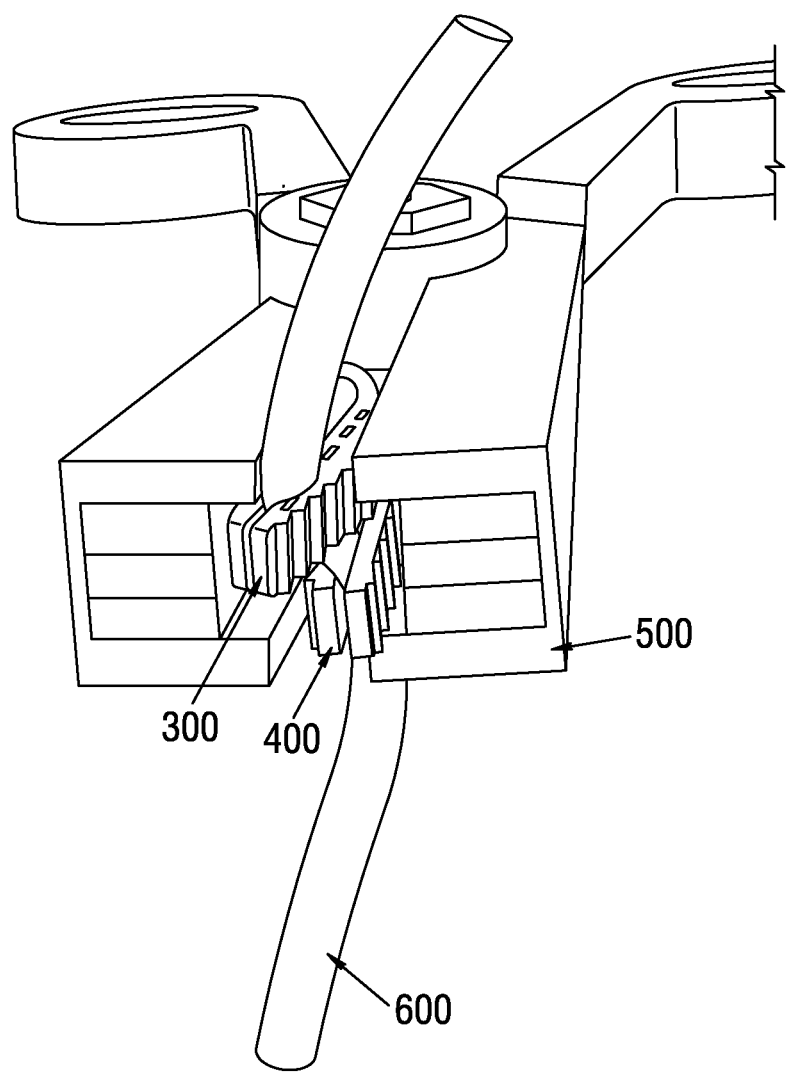
FIG. 3E is a fifth step in applying a surgical clip according to exemplary aspects of the present disclosure.
Figure 3F:
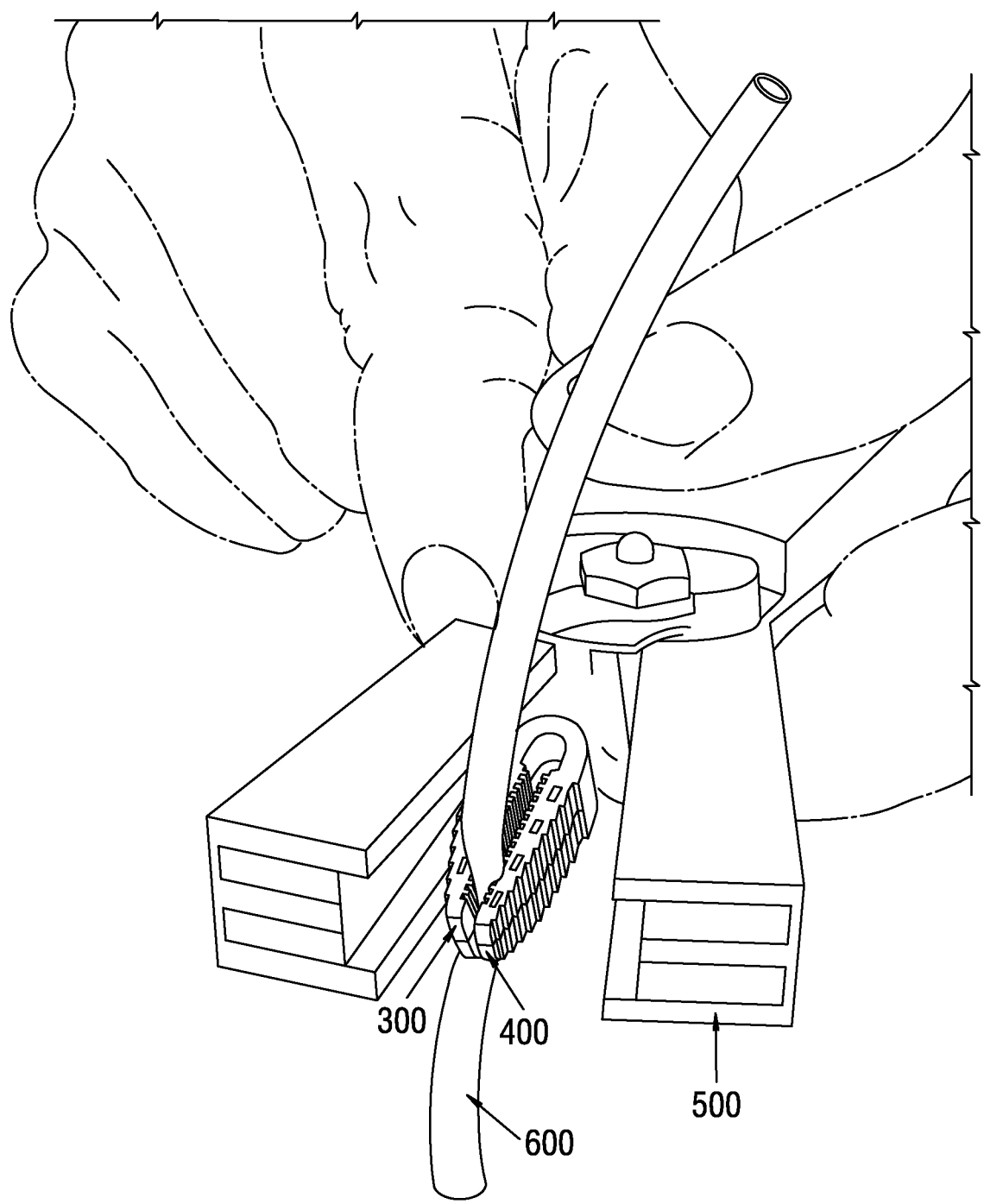
FIG. 3F is a sixth step in applying a surgical clip according to exemplary aspects of the present disclosure.
Figure 3G:
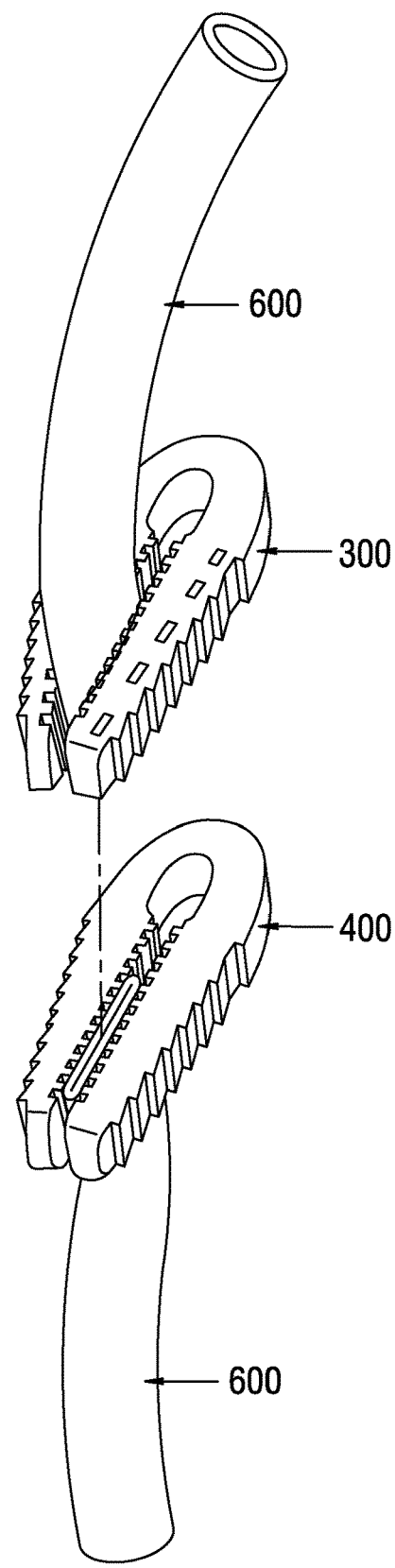
FIG. 3G is a seventh step in applying a surgical clip according to exemplary aspects of the present disclosure showing both clips on each end of a divided blood vessel.

FIG. 3A shows two surgical clips 300 and 400, such as those illustrated in FIG. 2H, being held in a clip applicator 500. This represents the first step in applying the surgical clips 300 and 400 to a blood vessel (not shown). The surgical clips 300 and 400 are deformed around the blood vessel 600 in a second step illustrated by FIG. 3B. In FIG. 3C the surgical clips 300 and 400 partially close around the blood vessel 600, and in FIG. 3D the surgical clips 300 and 400 are completely closed around the blood vessel 600. Additional force is applied to cause the surgical clips 300 and 400 to perform the scissoring action (FIG. 3E), and the clip applicator 500 is released in FIG. 3F showing that the blood vessel 600 has been cut and that a surgical clip 300 and 400 is attached to each cut end of the blood vessel 600. FIG. 3G illustrates a firmly applied clip 300 after the division of the blood vessel 600 has been completed.

FIG. 4A illustrates a surgical clip cross-section according to exemplary aspects of the present disclosure. In FIG. 4A, the cutting edge 202 of is the clip buried or shielded in the opposite clip leg 200 to avoid contact and possible damage to the surrounding tissue. FIG. 4B is another cross-section of a surgical clip whose cutting edge 202 is buried or shielded by the opposite clip leg to avoid contact and possible damage to the surrounding tissue. As can be appreciated, other surgical clip cross-sections are possible without departing from the scope of the present disclosure.

Figure 5A:
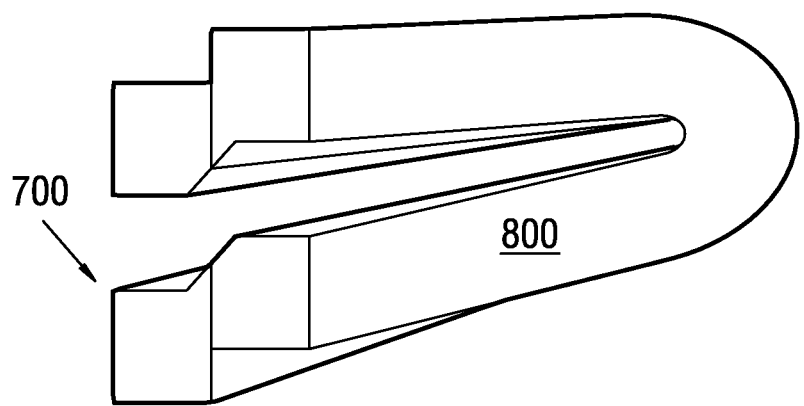
FIG. 5A illustrates a three-dimensional view of surgical clips according to exemplary aspects of the present disclosure.
Figure 5B:
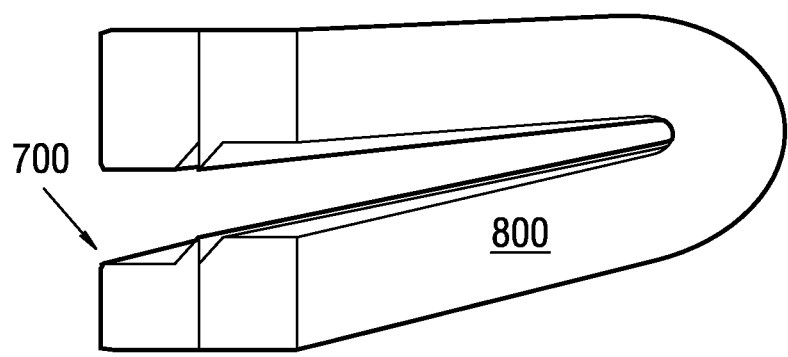
FIG. 5B illustrates another three-dimensional view of surgical clips according to exemplary aspects of the present disclosure.

FIGS. 5A and 5B illustrates two loading configurations of the surgical clips according to exemplary aspects of the present disclosure in order to prevent exposure of the cutting edges to surrounding tissue. As illustrated in FIG. 5A, the clips 700 and 800 are loaded at a slight offset to each other such that each clip shields the other clip's cutting blade. FIG. 5B illustrates how the cutting edges of the surgical clips 700 and 800 are exposed if loaded level to each other, risking injury to tissue during the placement of the clips on the blood vessel. Once in place, the clips can be brought level by the pressure exerted by the applicator as the surgical clips are deformed into their closed positions.

To the extent that the above descriptions may be deemed separate embodiments, such description in separate embodiments is made solely for the sake of clarity. One of ordinary skill would recognize that the inventive concepts described with reference to one embodiment are readily combinable with any and all inventive concepts described with reference to the other embodiments.

Moreover, the material from which the surgical clips described herein is not limiting upon the present disclosure. As such, the surgical clips may be made from metals, such as stainless steel, titanium, tantalunum, platinum, an alloy of metals, or made from polymer materials.

Obviously, numerous modifications and variations of the present invention are possible in light of the above teachings. It is therefore to be understood that within the scope of the appended claims, the invention may be practiced otherwise than as specifically described herein.

The invention claimed is:

1. A surgical clip for simultaneously cutting a blood vessel and controlling bleeding, the surgical clip comprising:
   two legs, each including a flat surface to hold the blood vessel, only one of the two legs including a cutting surface to cut the blood vessel; and
   a curved section configured to join the two legs,
   wherein the surgical clip is configured to, in conjunction with another surgical clip, simultaneously hold and cut the blood vessel through a scissoring action with the other surgical clip.

2. The surgical clip according to claim 1, wherein the cutting surface of the one of the two legs is offset relative to a center of the one of the two legs.

3. The surgical clip according to claim 1 wherein, on the one of the two legs, the cutting surface is adjacent to the flat surface.

4. The surgical clip according to claim 2, wherein, when the surgical clip is in a closed state, the cutting surfaces of the one of the two legs is configured to bypass a cutting surface of the other surgical clip in order to cut the blood vessel through the scissoring action.

5. The surgical clip according to claim 1, wherein, when the surgical clip is in a closed state, the flat surfaces of each of the two legs, are configured to occlude a lumen of the blood vessel.

6. The surgical clip according to claim 1, wherein the surgical clip is formed from a single piece of material.

7. The surgical clip according to claim 6, wherein the material is one of stainless steel, titanium, tantalunum, platinum, an alloy of metals, or a polymer material.

8. The surgical clip according to claim 6, wherein the material is absorbable by a body in which the surgical clip is installed.

9. A blood vessel cutting and clamping system, comprising:
   a pair of surgical clips configured to simultaneously cut and clamp the blood vessel, each of the pair of surgical clips including:
   two legs, each including a flat surface to hold the blood vessel, only one of the two legs including a cutting surface to cut the blood vessel, and
   a curved section configured to join the two legs; and
   the applicator configured to hold the pair of surgical clips in contact with each other and to apply pressure to deform the pair of surgical clips in order to cause the surgical clips to simultaneously hold and cut the blood vessel through a scissoring action between the pair of surgical clips.

10. The blood vessel cutting and clamping system according to claim 9, wherein the pair of surgical clips have a same cross-sectional profile.

11. The blood vessel cutting and clamping system according to claim 9, wherein the pair of surgical clips have different cross-sectional profiles.

12. The blood vessel cutting and clamping system according to claim 11, wherein the pair of surgical clips have cross-sectional profiles that are mirror images of each other.

13. The surgical clip according to claim 1, wherein outer surfaces of the two legs are textured to prevent slippage when held in an applicator.

* * * * *

UNITED STATES PATENT AND TRADEMARK OFFICE
CERTIFICATE OF CORRECTION

| | |
|---|---|
| PATENT NO. | : 11,439,405 B2 |
| APPLICATION NO. | : 16/539074 |
| DATED | : September 13, 2022 |
| INVENTOR(S) | : Michael Siegenthaler |

It is certified that error appears in the above-identified patent and that said Letters Patent is hereby corrected as shown below:

In the Specification

In Column 1, Line 24, delete "tantalunum" and insert -- tantalum --.
In Column 4, Line 35, delete "cross-sectional" and insert -- cross-sections --.
In Column 5, Line 59, delete "tantalunum" and insert -- tantalum --.

Signed and Sealed this
Tenth Day of January, 2023

Katherine Kelly Vidal
*Director of the United States Patent and Trademark Office*